US012642915B2

(12) United States Patent
Rounds et al.

(10) Patent No.: US 12,642,915 B2
(45) Date of Patent: Jun. 2, 2026

(54) NEEDLE-FREE INJECTOR DOSE SETTING APPARATUS AND METHODS

(71) Applicant: PharmaJet Inc., Golden, CO (US)

(72) Inventors: Nick Rounds, Golden, CO (US);
Joseph Kapushion, Golden, CO (US);
Chris Cappello, Golden, CO (US)

(73) Assignee: PharmaJet, Inc., Golden, CO (US)

( * ) Notice: Subject to any disclaimer, the term of this patent is extended or adjusted under 35 U.S.C. 154(b) by 659 days.

(21) Appl. No.: 18/104,975

(22) Filed: Feb. 2, 2023

(65) Prior Publication Data

US 2024/0261514 A1     Aug. 8, 2024

(51) Int. Cl.
| | |
|---|---|
| *A61M 5/32* | (2006.01) |
| *A61M 5/20* | (2006.01) |
| *A61M 5/31* | (2006.01) |
| *A61M 5/315* | (2006.01) |

(52) U.S. Cl.
CPC ........ *A61M 5/3243* (2013.01); *A61M 5/2033* (2013.01); *A61M 5/3155* (2013.01); *A61M 2005/206* (2013.01); *A61M 2005/3126* (2013.01)

(58) Field of Classification Search
CPC .............. A61M 5/3243; A61M 5/2033; A61M 5/3155; A61M 2005/206; A61M 2005/3126
See application file for complete search history.

(56) References Cited

U.S. PATENT DOCUMENTS

| | | |
|---|---|---|
| 7,090,662 B2 | 8/2006 | Wimpenny et al. |
| 7,316,670 B2 | 1/2008 | Graf et al. |
| 8,197,450 B2 | 6/2012 | Glejbol et al. |
| 8,500,701 B2 | 8/2013 | Kirchhofer |
| 8,545,456 B2 | 10/2013 | Kirchhofer et al. |
| 8,641,683 B2 | 2/2014 | Glejbol et al. |
| 8,647,309 B2 | 2/2014 | Harms et al. |
| 8,663,167 B2 | 3/2014 | Bartha |
| 8,808,251 B2 | 8/2014 | Raab et al. |
| 8,840,591 B2 | 9/2014 | Raab et al. |
| 8,939,945 B2 | 1/2015 | Veasey et al. |
| 9,089,652 B2 | 7/2015 | Nzike et al. |
| 9,254,364 B2 | 2/2016 | Raab et al. |
| 9,327,082 B2 | 5/2016 | Kouyoumjian et al. |
| 9,381,306 B2 | 7/2016 | Hiles |

(Continued)

FOREIGN PATENT DOCUMENTS

| | | |
|---|---|---|
| EP | 2274032 B1 | 8/2012 |
| EP | 2482895 B1 | 8/2013 |

(Continued)

*Primary Examiner* — Dung T Ulsh
(74) *Attorney, Agent, or Firm* — Jones Day

(57) ABSTRACT

A needle-free injector including dose setting apparatus. The needle-free injector includes a hammer housing, a mainspring positioned within the hammer housing, and a hammer assembly engaged with the mainspring. The hammer assembly may include a hammer sleeve and a hammer engaged with the hammer sleeve, where the engagement between the hammer sleeve and the hammer provides for a forward or rearward position of the hammer with respect to the hammer sleeve be changed to select an injection dose from two or more available injection doses. Additional embodiments include methods of varying or setting the dose delivered by a needle-free injector.

15 Claims, 14 Drawing Sheets

(56)            References Cited

U.S. PATENT DOCUMENTS

| | | | |
|---|---|---|---|
| 9,393,368 B2 | 7/2016 | Nzike et al. | |
| 9,457,152 B2 | 10/2016 | Raab et al. | |
| 9,486,587 B2 | 11/2016 | Strehl et al. | |
| 9,539,396 B2 | 1/2017 | Raab et al. | |
| 9,592,348 B2 | 3/2017 | Strehl et al. | |
| 9,629,962 B2 | 4/2017 | Strehl et al. | |
| 9,700,678 B2 | 7/2017 | Smith et al. | |
| 9,717,859 B2 | 8/2017 | Harms et al. | |
| 9,731,079 B2 | 8/2017 | Plumptre | |
| 9,750,888 B2 | 9/2017 | Raab et al. | |
| 9,795,744 B2 | 10/2017 | Giambattista et al. | |
| 9,802,004 B2 | 10/2017 | Raab et al. | |
| 9,849,250 B2 | 12/2017 | Smith et al. | |
| 9,974,906 B2 | 5/2018 | Nzike et al. | |
| 10,232,119 B2 | 3/2019 | Raab et al. | |
| 10,286,154 B2 | 5/2019 | Strehl et al. | |
| 10,286,158 B2 | 5/2019 | Harms et al. | |
| 10,456,528 B2 | 10/2019 | Plumptre | |
| 2009/0275916 A1* | 11/2009 | Harms .................... | A61M 5/24 |
| | | | 604/211 |
| 2015/0238699 A1 | 8/2015 | Butler et al. | |
| 2018/0001025 A1 | 1/2018 | Sarkinen et al. | |
| 2018/0236175 A1 | 8/2018 | Nzike et al. | |

FOREIGN PATENT DOCUMENTS

| | | | |
|---|---|---|---|
| EP | 2373363 B1 | 3/2014 | |
| EP | 2482887 B1 | 7/2014 | |
| EP | 1877121 B1 | 9/2015 | |
| EP | 2637723 B1 | 7/2016 | |
| EP | 3130370 A1 | 2/2017 | |
| EP | 2376148 B1 | 4/2018 | |
| EP | 2926850 B1 | 4/2018 | |
| EP | 3335749 B1 | 10/2019 | |

* cited by examiner

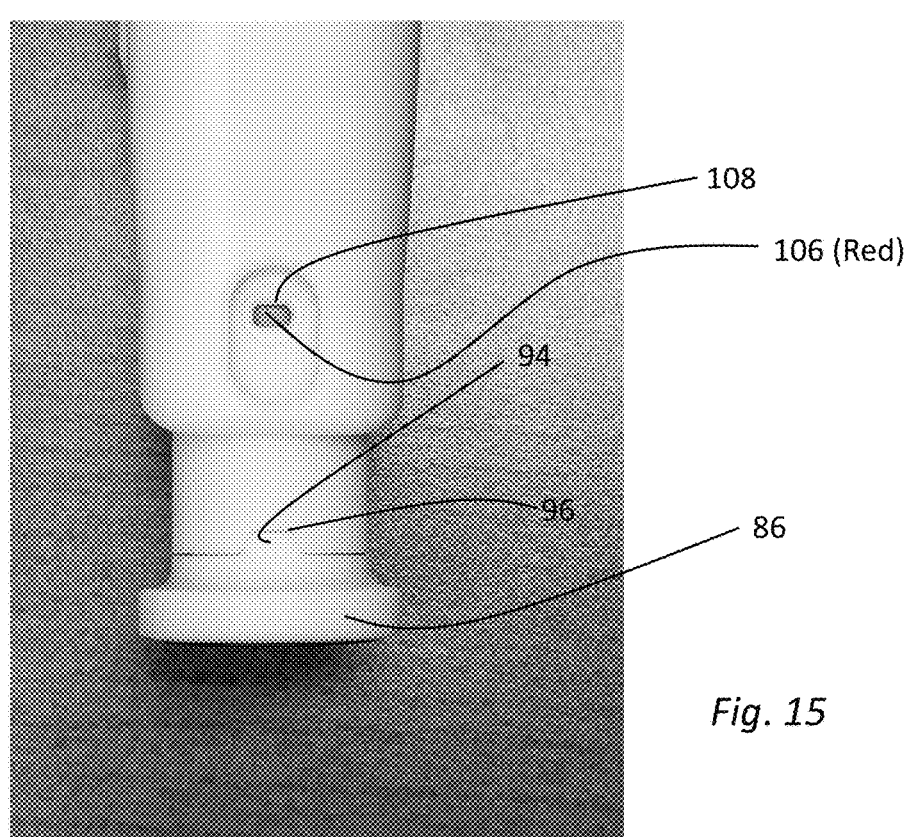
*Fig. 15*
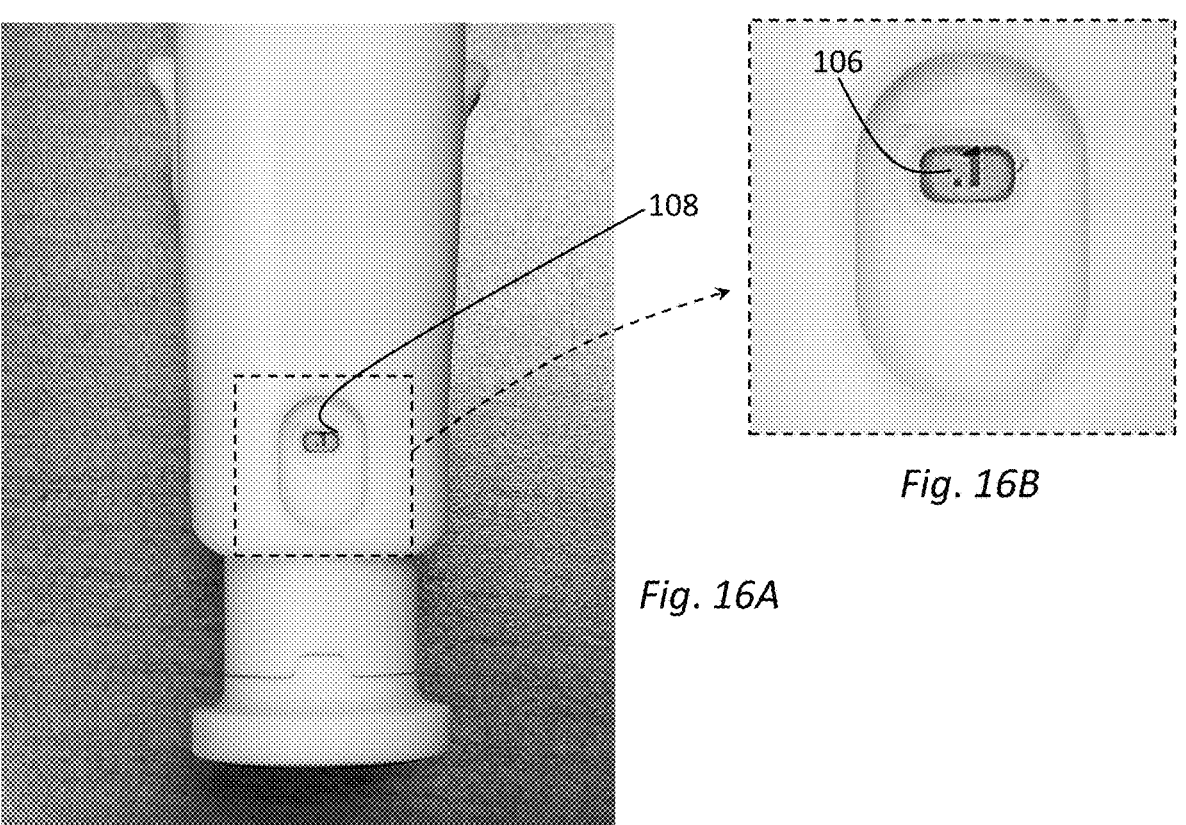
*Fig. 16B*
*Fig. 16A*

114

106

116

NEEDLE-FREE INJECTOR DOSE SETTING APPARATUS AND METHODS

FIELD OF THE INVENTION

The present disclosure relates to systems, apparatus, and methods for setting the dose of an injectable material delivered by a needle-free injector.

BACKGROUND OF THE INVENTION

The advantages of needle-free injection devices have been recognized for some time. Some of the advantages of needle-free devices and methods include the absence of a needle which can intimidate a patient and also present a hazard to healthcare workers. In addition, injection using a needle may increase the risk of cross-contamination between patients. Furthermore, with an injection device that employs a needle there is substantial risk of needle breakage in the tissue of a human or animal patient. The injection jet generated by a needle-free device is generally quicker and more preferred than an injection provided by a hypodermic needle device.

Many variations of pneumatic, electronic, or spring activated needle-free injection devices have been designed to provide a single injection because of the noted and other advantages. Typical modern needle-free injectors are designed to use with a single-use and/or disposable needle-free syringe to minimize the risk of cross-infection. A single use and/or disposable needle-free syringe will have structure permitting the needle-free syringe to be attached to the corresponding injector, easily ejected from the injector, and disposed of or recycled. Some needle-free injectors are integrated with a needle-free syringe and the entire device is single-use and disposable. Typically, each syringe is designed to hold a specific quantity of an injectable material, and the corresponding injector is designed to fully expel that specific quantity of injectable material during an injection. Therefore, it is difficult or impossible with many needle-free injector/syringe combinations to select, change, or vary the quantity of injectable material delivered between injections.

It is sometimes beneficial to vary from the standard dose of a therapeutic injectable material. For example, if the patient is a child, is very small, is very large, or has medical conditions which affect dosing. In many cases, the user must select an entirely different needle-free injector/syringe combination if a variation from the standard dose provided by a specific needle-free injector/syringe combination is desired.

The embodiments disclosed herein are directed toward overcoming one or more of the above problems.

SUMMARY OF THE EMBODIMENTS

One general aspect disclosed herein is a needle-free injector including dose setting apparatus. The needle-free injector includes a hammer housing, a mainspring positioned within the hammer housing, and a hammer assembly engaged with the mainspring. The hammer assembly may include a hammer sleeve and a hammer engaged with the hammer sleeve, where the engagement between the hammer sleeve and the hammer provides for a forward or rearward position of the hammer with respect to the hammer sleeve be changed to select an injection dose from two or more available injection doses.

In some implementations, the engagement between the hammer sleeve and the hammer is a threaded engagement. The hammer sleeve may include a spring interface shoulder.

The hammer may include a hammer stopping block. The hammer housing may include a forward wall contacted by the hammer stopping block when the needle-free injector is discharged. This embodiment may also include a control assembly to cause the forward or rearward position of the hammer with respect to the hammer sleeve to change. The control assembly can be a dose selector knob, such that rotation of the dose selector knob causes the hammer to rotate at the threaded engagement with respect to the hammer sleeve. The control assembly may include an indexing structure that becomes engaged to limit rotation of the dose selector knob when the dose selector knob is rotated through a defined angle of rotation. The needle-free injector may also include a status indicator and window through which the status indicator may be viewed. The status indicator can include indicia of the arming status of the needle-free injector, the selected dose to be delivered by the needle-free injector, other information, or combinations of information.

Other embodiments disclosed herein include methods of setting or selecting a dose to be delivered by a needle-free injector as described above. Dose setting steps include manipulating the engagement between the hammer sleeve and the hammer to cause a forward or rearward position of the hammer with respect to the hammer sleeve to be changed to select an injection dose from two or more available injection doses.

BRIEF DESCRIPTION OF THE DRAWINGS

FIG. 15 is a plan view of a dose setting control apparatus as disclosed herein.

FIG. 16A is a plan view of the dose setting control apparatus of FIG. 15, with alternative indicia viewable through the window.

FIG. 16B is a view of the dose setting control apparatus of FIG. 16A highlighting the window and indicia elements.

DETAILED DESCRIPTION OF THE INVENTION

Figure 1:
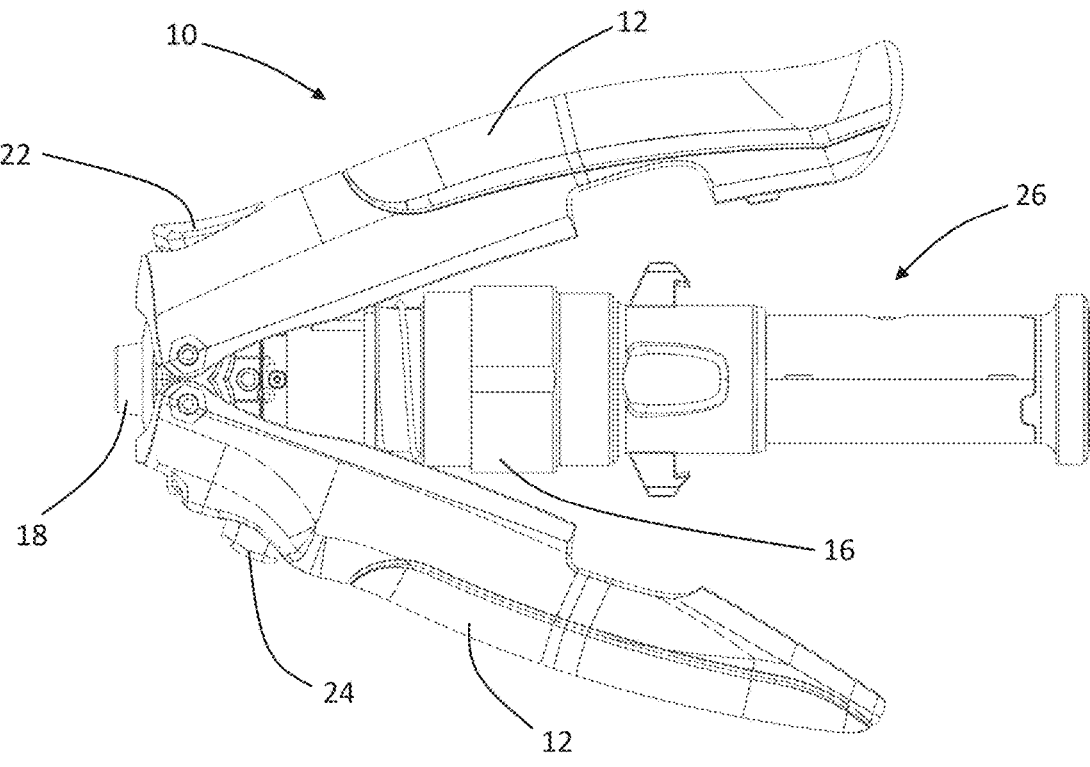
FIG. 1 is a front elevation view of a representative needle-free injector with dose setting apparatus as disclosed herein.
Figure 2:
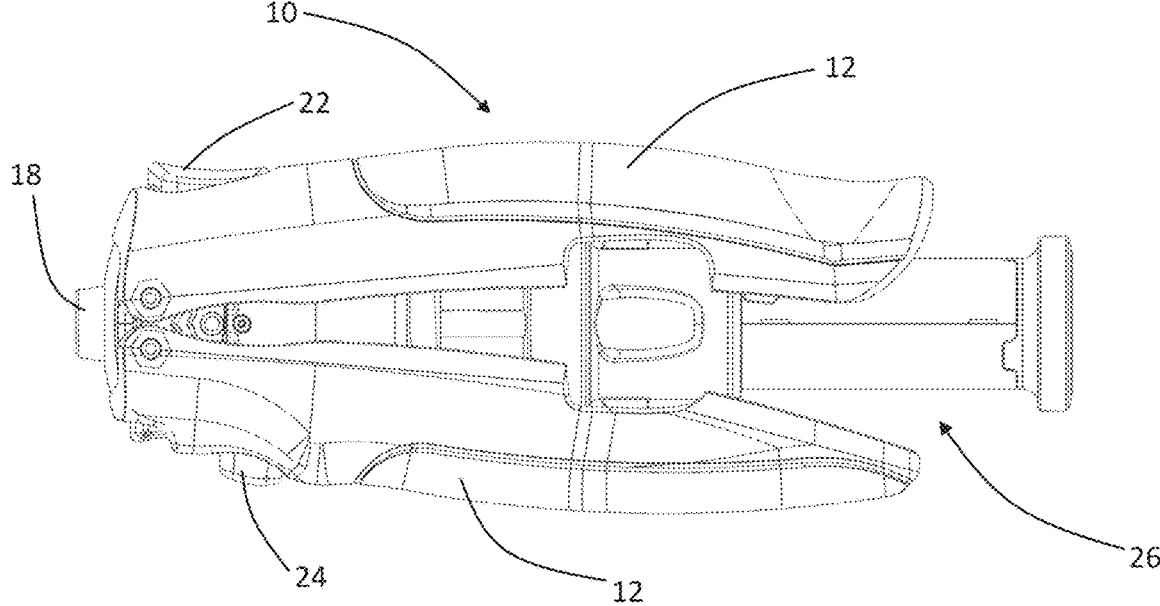
FIG. 2 is a front elevation view of the needle-free injector of FIG. 1 in an armed configuration.
Figure 3:
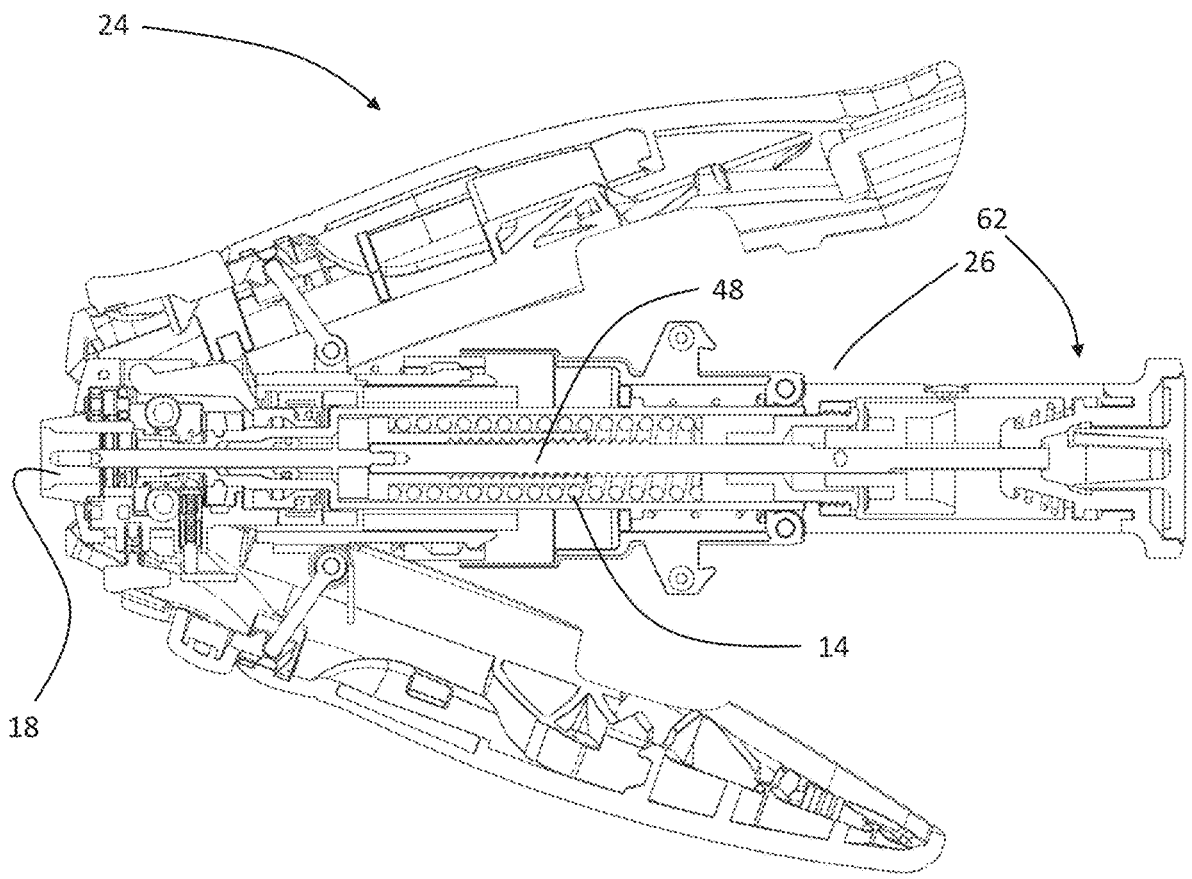
FIG. 3 is a vertical sectional view of the needle-free injector of FIG. 1, sectioned along the longitudinal centerline of the injector.

In the following description, for the purposes of explanation, numerous specific details are set forth to provide a thorough understanding of the described embodiments. It will be apparent to one skilled in the art, however, that other embodiments may be practiced without some of these specific details. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

A representative needle-free injector 10 including the dose-setting apparatus disclosed herein is shown in FIGS. 1-6. Many needle-free injectors include apparatus configured to drive the plunger of a needle-free syringe toward the syringe nozzle to expel a vaccine, therapeutic medicament, or other liquid injectable substance contained within the needle-free syringe. Furthermore, the injector apparatus must expel the injectable substance with sufficient force to inject the injectable substance into a patient's tissues without an intervening needle. Known needle-free injectors can be configured to inject into intradermal layers, intramuscular tissue, or subcutaneous tissue layers. Some needle-free injectors are configurable to selectively inject into more than one layer of tissue. The dose setting apparatus and methods disclosed herein may be implemented with a needle-free injector sized or configured to deliver an injectable substance into any tissue layer.

In addition, various mechanisms are known to provide the force necessary to expel the injectable substance from the needle-free syringe. Known needle-free injector driving mechanisms include compression springs, sources of compressed gas and electric solenoids. The dose setting apparatus and methods disclosed herein may be implemented with a needle-free injector relying upon any power source including but not limited to springs, compressed gas, or electric power sources.

The specific needle-free injector 10 shown in FIGS. 1-6 is a spring-driven injector configured to inject into intradermal layers. As described in detail herein, the representative injector includes apparatus permitting the dose of the injectable substance delivered by the injector 10 to be selected or controlled by a user. In certain embodiments, the possible doses selected are infinitely variable between two endpoints. For example, an injector 10 configured for intradermal injection may be configured to deliver an infinitely variable dose selected from between the endpoints of 0.02 mL and 0.1 mL. An alternative device configured for intramuscular or subcutaneous injection may be configured to deliver an infinitely variable dose selected from between the endpoints of 0.25 mL and 0.5 mL.

Alternative injectors 10 may include indexing apparatus facilitating the selection and delivery of specific incremental doses between the endpoints. For example, an injector configured for intradermal use may be configured to allow a user to select and deliver doses of 0.02 mL, 0.03 mL, 0.04 mL, 0.05 mL, 0.06 mL, 0.07 mL, 0.08 mL, 0.09 mL, and 0.1 mL. An alternative injector 10 may be configured for injection to intramuscular or subcutaneous tissue and be configured to allow a user to select doses of 0.25 mL and 0.5 mL. The representative dose ranges and increments described above are not intended to be limiting upon the scope of the disclosure. The dose setting mechanism and methods described herein can be scaled and implemented to provide any desired dose within any selected endpoints.

In general, the representative injector 10 of FIGS. 1-6 is prepared for use by installing a mating needle-free syringe, arming the injector by compressing the mainspring 14, delivering an injection and then ejecting the syringe. To accomplish these fundamental tasks, the injector 10 includes handles 12 operated by a user to compress the mainspring 14 and arm the injector 10 before an injection. The handles 12 are attached to a housing or injector body 16. Portions of the injector define a socket 18 configured to receive an appropriate needle-free syringe 20, as shown in the detailed views of FIG. 4 and FIG. 5. A typical injector 10 will also include various controls used to prepare for and deliver an injection. Representative controls may include, but are not limited to an activation/syringe loading button 20 and a syringe ejection button 22. Additional detail concerning an embodiment of an intradermal injector is included in co-owned U.S. Pat. No. 9,433,735 entitled "Needle-Free Intradermal Injection Device," the full disclosure of which is incorporated herein by reference for all matters shown therein. Additional detail concerning an embodiment of an intramuscular/subcutaneous injector is included in co-owned U.S. Pat. No. 9,408,972 entitled "Needle-Free Injection Device," the full disclosure of which is incorporated herein by reference for all matters shown therein.

Figures 4, 5:
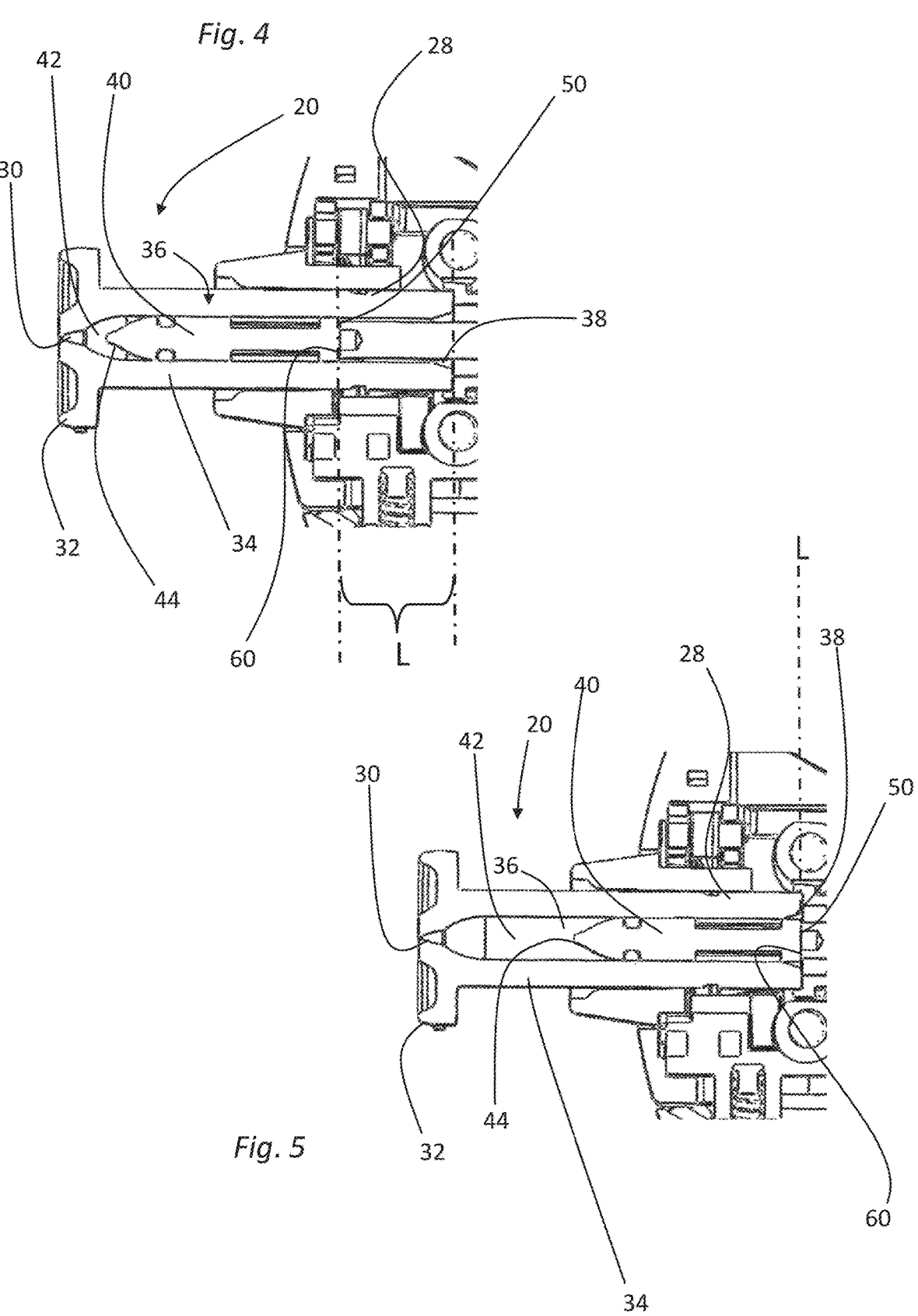
FIG. 4 is a vertical sectional view of the forward portions of the needle-free injector of FIG. 1, sectioned along the longitudinal centerline of the injector, with a needle-free syringe installed and the dose setting apparatus set to deliver a minimum dose.
FIG. 5 is a vertical sectional view of the forward portions of the needle-free injector of FIG. 1, sectioned along the longitudinal centerline of the injector, with a needle-free syringe installed and the dose setting apparatus set to deliver a maximum dose.

The injector 10 also includes a dose setting apparatus 26 described in detail below. The embodiments of dose setting apparatus 26 disclosed herein are configured to work with replaceable and/or disposable needle-free syringes 20. The dose setting apparatus 26 provides for the dose to be delivered by an injector 10 and needle-free syringe 20 combination to be selected from multiple possible doses without requiring any change to the mechanical structure of the syringe 20. Thus, the same size and type of syringe may be used at any selected dose. As illustrated in FIGS. 4 and 5, a representative needle-free syringe 20 typically includes indexing features 28 configured to engage with the socket 18 of an injector 10 prior to an injection. Opposite the indexing features 28 are a nozzle 30 and skin tensioning ring 32 which in use are placed against a patient's skin. The syringe body 34 defines an internal cavity 36 extending from the nozzle 30 to an opening 38 opposite the nozzle 30. A plunger 40 is positioned within the internal cavity 36. When the injector 10 is armed and ready to deliver an injection, a dose space 42 having a specific volume is defined within the internal cavity 36 between the nozzle 30 and a forward surface 44 of the plunger 40. As used throughout this disclosure, the direction "forward" is defined to mean toward the nozzle end of a needle-free syringe 20 or toward the syringe socket end of an injector 10. The direction "rearward" is defined as being away from the nozzle/socket end of the injector 10 and syringe 20.

As can be seen by comparing FIG. 4 with FIG. 5, the dose space 42 can be caused to have a greater or lesser volume by the positioning of the plunger 40 within the internal cavity 36 prior to an injection. Prior to injection, the dose space 42 is filled with an injectable substance. The various embodiments of dose setting apparatus 26 disclosed herein can be used to set a selected dose space 42, and therefore select the dose of an injectable substance delivered to a patient. As one non-limiting example, the volume in the dose space 42 illustrated in FIG. 4 is 0.02 mL while the volume in the dose space 42 illustrated in FIG. 5 is 0.1 mL. These doses are deliverable from the same injector 10, using mechanically identical needle-free syringes 20. Furthermore, an injector 10 including the dose setting apparatus 26 can properly deliver the selected dose through intervening tissue layers without using a hypodermic needle. Attributes of a proper dose delivery include, but are not limited to, injection to the desired tissue layer at any dose, minimal waste of the injectable substance, and relatively easy use, which minimizes the risk of operator error during an injection or during dose setting steps.

Figure 7:
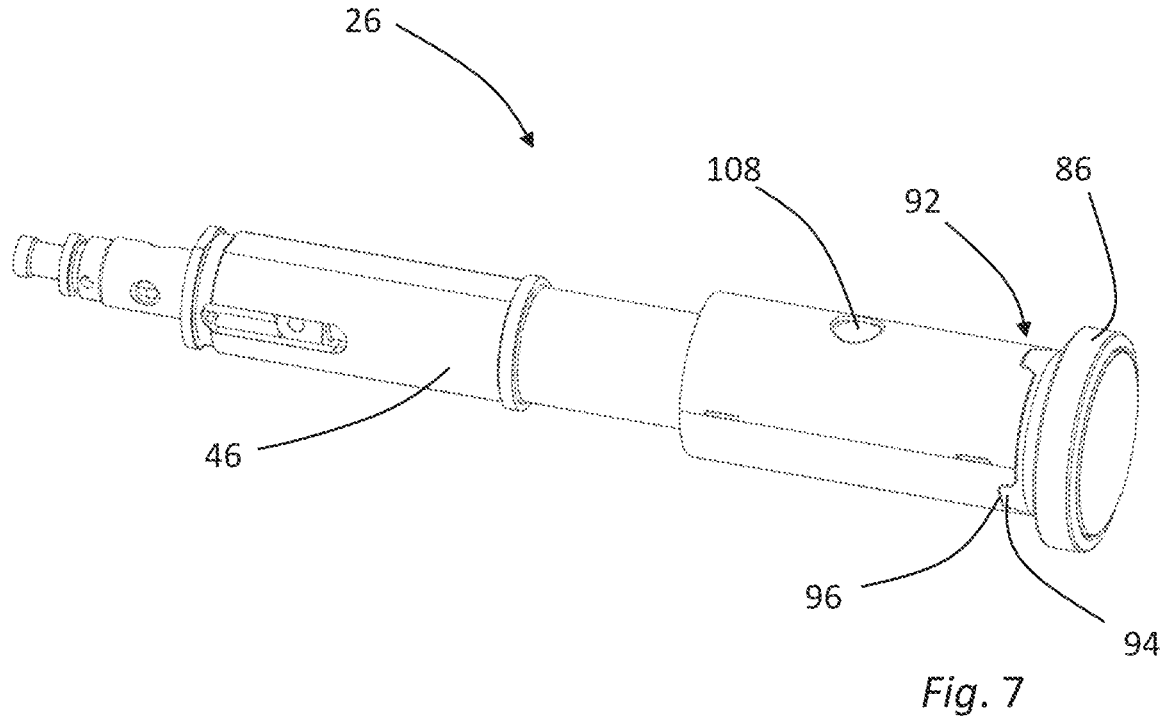
FIG. 7 is a perspective view of a dose setting apparatus as disclosed herein.
Figure 8:
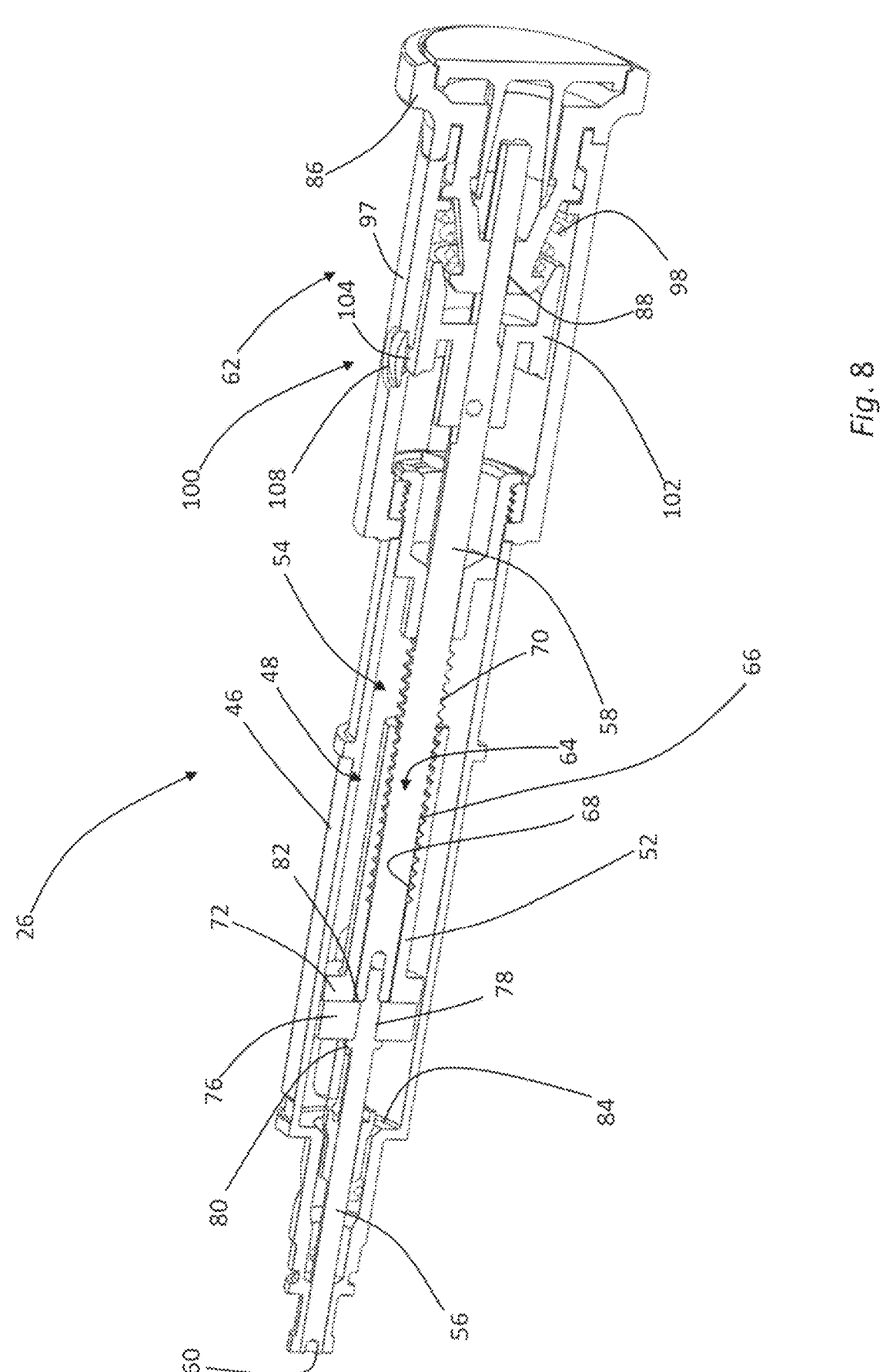
FIG. 8 is a vertical sectional view of the dose setting apparatus of FIG. 7, sectioned along the longitudinal centerline of the dose setting apparatus.

A representative dose setting apparatus 26 is illustrated in FIG. 7 and FIG. 8. The dose setting apparatus 26 includes a hammer housing 46 which supports and houses various internal components. The hammer housing 46 may be a unitary structure or may be composed of any number of multiple substructures. The hammer housing 46 as defined herein is not limited to any specific structure other than being a structure that at least partially contains or houses the hammer assembly 48.

In the FIG. 1-6 injector 10 embodiment a mainspring 14 surrounds and contacts the hammer assembly 48. Thus, the mainspring 14 is also located within the hammer housing 46 in the illustrated embodiment. As noted above, the dose setting apparatus 26 can be utilized in an injector which utilizes compressed gas or an electric solenoid to provide the force necessary for a needle-free injection. In such an implementation, the hammer assembly 48 would include or would be in contact with a gas or solenoid piston, or other structure, configured to be forced forward by expanding gas or electromagnetic energy to drive an injection.

The hammer assembly 48 of FIG. 8 includes various components described in detail below. In general, however, the hammer assembly 48 is a piston-like apparatus engaged with the mainspring 14 or other power source. The hammer assembly 48 is also in contact with the rearward surface 50 of a syringe plunger 40 prior to an injection. During an injection, the injector 10 is operated to release the energy previously stored in the mainspring 14 to drive the hammer assembly 48 forward, thereby forcing the plunger 40 forward within the syringe 20 causing an injection through the nozzle 30.

Figure 6:
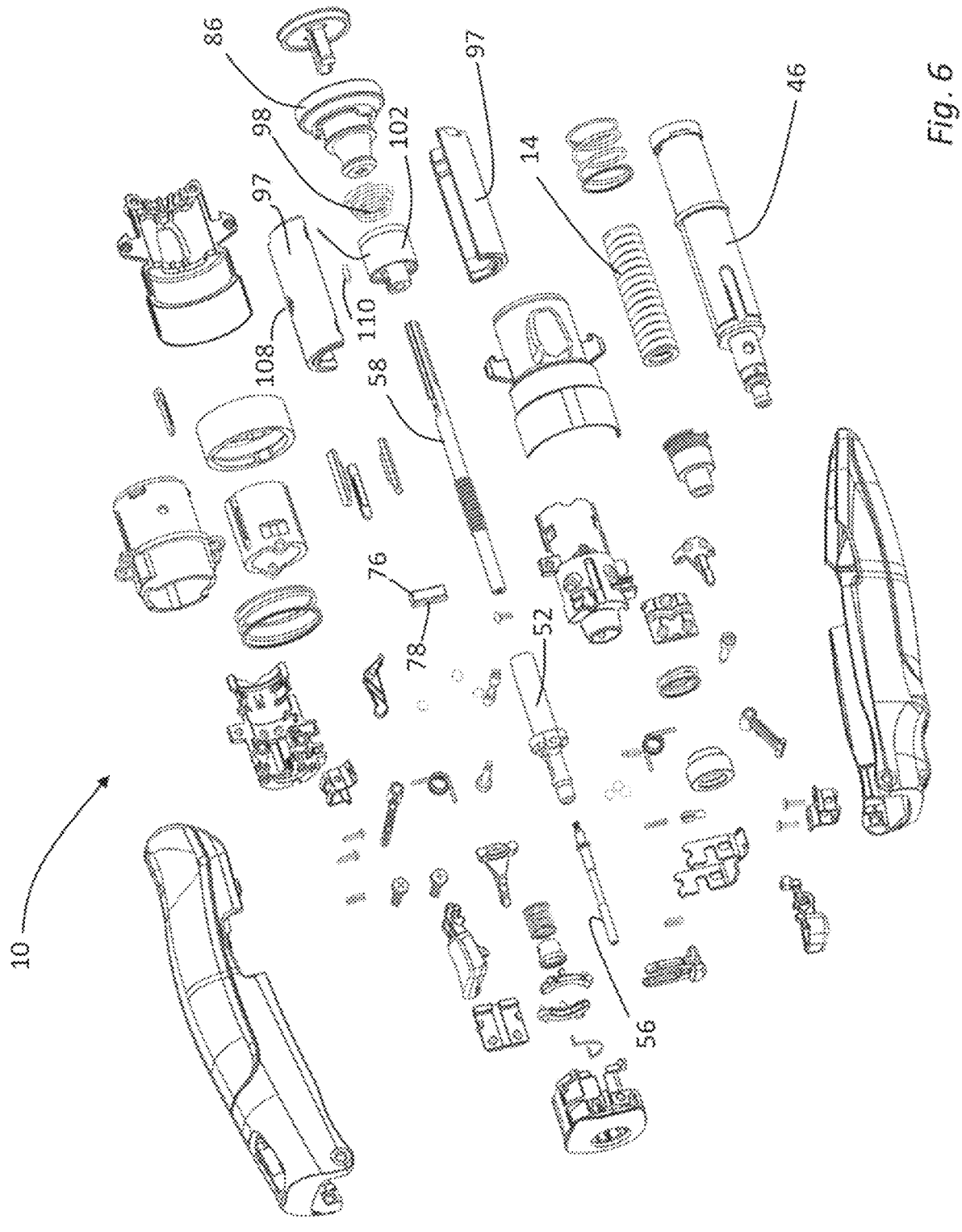
FIG. 6 is an exploded view of the needle-free injector of FIG. 1.
Figures 9A, 9B, 9C:
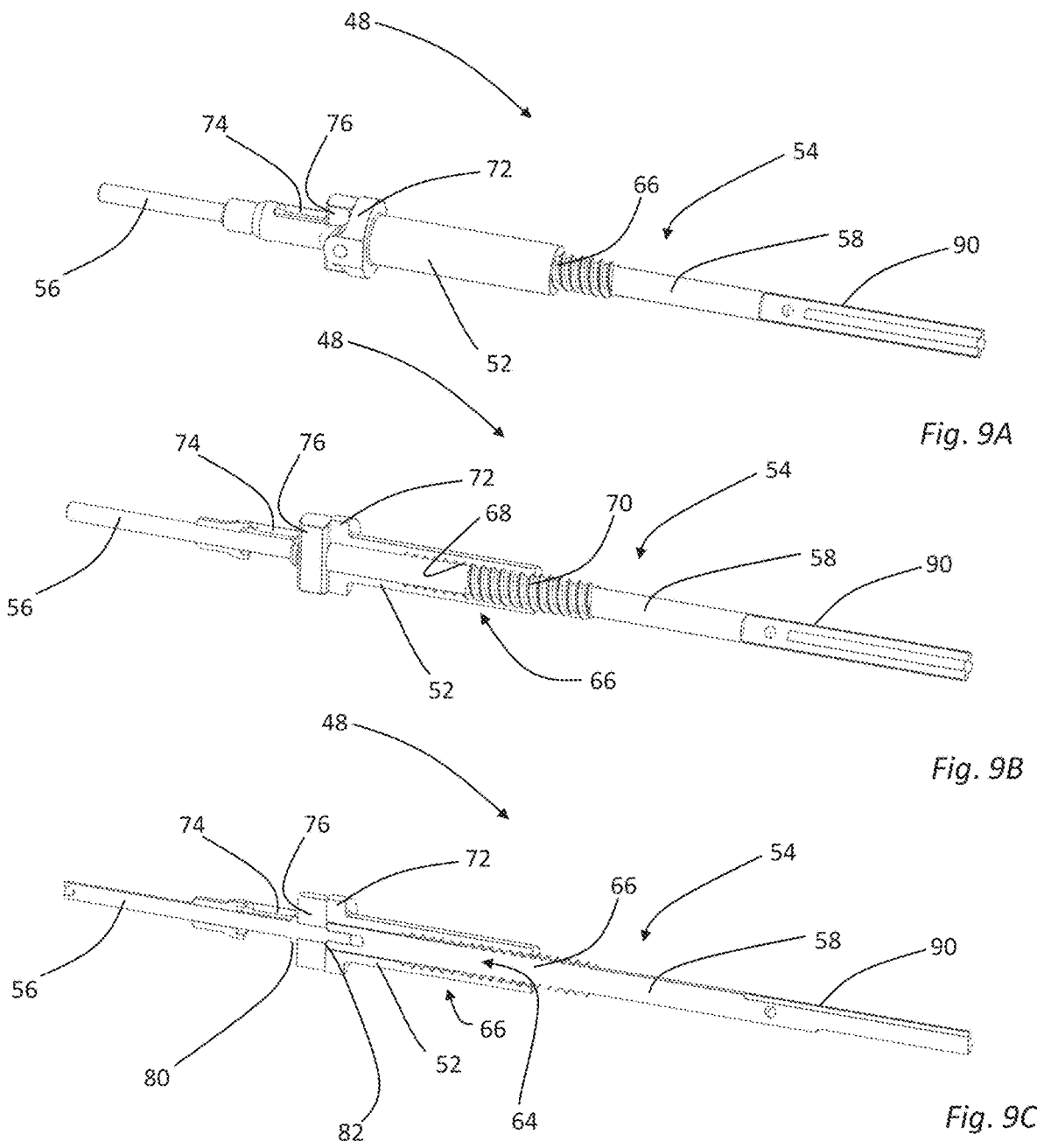
FIG. 9A is a perspective view of a hammer assembly as disclosed herein
FIG. 9B is a combination sectional and perspective view of the hammer assembly of FIG. 9A.
FIG. 9C is a vertical sectional view of the hammer assembly of FIG. 9A, sectioned along the longitudinal centerline of the hammer assembly.

A representative hammer assembly 26 is illustrated in FIGS. 9A, 9B, and 9C. The hammer assembly includes a hammer sleeve 52 engaged with a hammer 54. As best shown in the exploded view of FIG. 6 the hammer 54 includes at least a forward extension 56 and a rearward extension 58. The forward extension 56 and rearward extension 58 may be co-formed in certain hammer 54 embodiments, or as illustrated in FIG. 6, the forward extension 56 and rearward extension 58 may be formed as separate components which are joined together at a threaded junction or by other means during assembly. When an injector 10 is armed and ready for an injection, a forward surface 60 of the forward extension 56 contacts the rearward surface 50 of the syringe plunger 40. In addition, portions of the rearward extension 58 contact the control assembly 62 of the dose setting apparatus 26.

The hammer 54 extends through a lengthwise bore 64 defined by the hammer sleeve 52. Thus, the hammer 54 can be moved forward or rearward with respect to the hammer sleeve 52. Precise forward or rearward movement of the hammer 54 with respect to the hammer sleeve 52 can be accomplished with a threaded engagement 66 between the hammer 54 and hammer sleeve 52. For example, the hammer sleeve 52 may include female threads 68 along the bore 64 extending through the hammer sleeve 52. The hammer 54 may include corresponding male threads 70 around an exterior surface. In the illustrated embodiment, the male threads 70 are formed around an exterior surface of the rearward extension 58. In an alternative embodiment the male threads 70 may be formed around an exterior surface of the forward extension 56. In a threaded embodiment, rotation of the hammer 54 with respect to the hammer sleeve 52 provides for precise adjustment of the forward or rearward position of the hammer 54 with respect to the hammer sleeve 52. Other mechanisms for the adjustment of the forward or rearward position of the hammer 54 with respect to the hammer sleeve 52 are within the scope of this disclosure. For example, the relative positions of the hammer 54 and hammer sleeve 52 may be adjusted with a sliding engagement plus lock screw or other locking mechanism, or with a ratchet mechanism.

The hammer sleeve 52 includes an engagement with the mainspring. In the illustrated embodiment, the engagement with the mainspring is a spring interface shoulder 72. The illustrated spring interface shoulder 72 is a flange formed in an exterior surface of the hammer sleeve 52. The spring interface shoulder 72 could be implemented with a separate part, for example a bushing and set screw assembly, spring engagement pin, or the like. The spring interface shoulder 72 is at all times engaged with the forward end of the mainspring 14.

As best viewed in FIG. 9A, the hammer sleeve 52 also includes a stabilizing slot 74 which receives a hammer stopping block 76. The hammer stopping block 76 is engaged with the hammer 54 such that the lengthwise position of the hammer stopping block 76 is locked to the hammer, causing the stopping block 76 to move forward or rearward with the hammer 54 while remaining within the stabilizing slot 74 of the hammer sleeve 52. In a threaded hammer assembly 48 embodiment, the hammer 54 must be free to rotate with respect to the hammer sleeve 52, therefore the hammer stopping block 76 includes a central channel 78 through which the hammer 54 extends. The hammer 54 is not bonded to the central channel 78, therefore the hammer 54 may rotate around its center axis within the central channel 78. The hammer stopping block 76 is captured at a lengthwise position on the hammer 54 between a flange 80 and a forward shoulder 82 of the rearward extension 58. Thus, when the hammer 54 is rotated within the hammer sleeve 52, the hammer stopping block 76 does not rotate but moves forward and rearward within the hammer sleeve 52, while supported by the stabilizing slot 74.

As described in more detail below, the hammer stopping block 76 contacts a forward wall 84 of the hammer housing 46 at the completion of an injection. Thus, contact between the hammer stopping block 76 and the forward wall 84 stops forward movement of the entire hammer assembly 48 at the end of an injection.

The dose setting apparatus also includes a control assembly 62. The control assembly 62 is used to adjust the forward or rearward position of the hammer 54 within the hammer sleeve 52. The illustrated control assembly 62 includes a dose selector knob 86 engaged with the hammer 54. The illustrated dose selector knob 86 includes a central socket 88 defined by the dose selector knob 86 to mate with splines 90, or other structures on the hammer 54 to ensure that the dose selector knob 86 rotationally locked to the hammer 54. The hammer 54 and dose selector knob 86 are not otherwise bonded together. Thus, the hammer 54 can be moved freely forward or rearward with respect to the dose selector knob 86 while maintaining rotational engagement. As described in detail below, certain embodiments of dose selector knob 86 may also be separately moved rearward and forward while maintaining rotational engagement with the hammer 54.

The dose selector knob 86 may include or be associated with an indexing structure 92. One example of indexing structure 92 includes the extensions 94 from the dose selector knob 86 which mate with corresponding gaps 96 defined in a corresponding control housing element 97 as shown in FIGS. 6 and 7. Other possible indexing structure embodiments include, but are not limited to, mating radial splines, other mating shapes that can be readily engaged and disengaged, pin and socket assemblies, opposing magnets, and the like. Any indexing structure 92 assures that the dose selector knob 86 cannot easily be rotated when the indexing structure 92 is engaged. On the contrary, the dose selector knob 86 can be readily rotated when disengaged from the indexing structure 92. Furthermore, the dose selector knob 86 can be rotated in defined steps having a pre-defined rotational angle as determined by the indexing structure 92. Alternatively, any indexing structure 92 may be omitted so that the dose selector knob 86 is infinitely adjustable.

In an embodiment including indexing structures 92, the dose selector knob 86 may be biased forward by a spring 98 such that the indexing structures 92, for example extensions 94 and gaps 96, are biased into contact when the dose selector knob 86 is rotated to the proper angle for engagement. In this configuration, the dose selector knob 86 must be pulled rearward against the bias provided by spring 98 to disengage the indexing structures 92 before the dose selector knob 86 can be rotated to a different angle. The indexing structures 92 and/or biasing spring 98 provide security against inadvertent rotation of the dose selector knob 86.

The control assembly 62 may also include a status indicator 100 defined by or attached to the hammer. In the illustrated embodiment, the status indicator is a substantially cylindrical status sleeve 102 bonded to the rearward extension 58 of the hammer 54 such that the cylindrical status sleeve 102 rotates and moves forward and rearward with the hammer 54. The cylindrical status sleeve 102 includes an outward facing surface 104 that can be marked with indicia 106 related to device status. As described in detail below, the indicia 106 may be viewed by a user through a window 108 in the housing element 97. In some embodiments the window 108 will include a magnifying lens 110. Alternatively, the indicial can be directly visible if there are no overlaying housing elements.

The above-described apparatus may be used to select, adjust, or otherwise set a dose to be delivered by a needle-free injector. As noted above, it is desirable for a user to be able to set or select a dose for an injection without having to select among various dose-specific syringes. The embodiments disclosed herein permit dose selection and dose delivery using replaceable or disposable syringes which are otherwise structurally identical. It is also advantageous to set or select a dose without unnecessarily wasting the therapeutic injectable substance. Finally, it is important that the mainspring 14 be properly compressed according to design parameters for any selected dose to ensure complete and proper injection.

As shown by comparing FIG. 4 and FIG. 5, the dose to be delivered from an otherwise structurally identical syringe is defined by the dose space 42 between the forward surface 44 of the needle-free syringe plunger 40 and the nozzle 30. In the illustrated example, the representative dose space 42 of FIG. 4 is approximately the minimum dose (for example 0.02 mL) achievable with the illustrated injector 10. The representative dose space 42 of FIG. 5 is approximately the maximum dose (for example 0.1 mL) achievable with the injector 10. Intermediate doses would be defined by intermediate plunger positions.

Figures 10A, 10B:
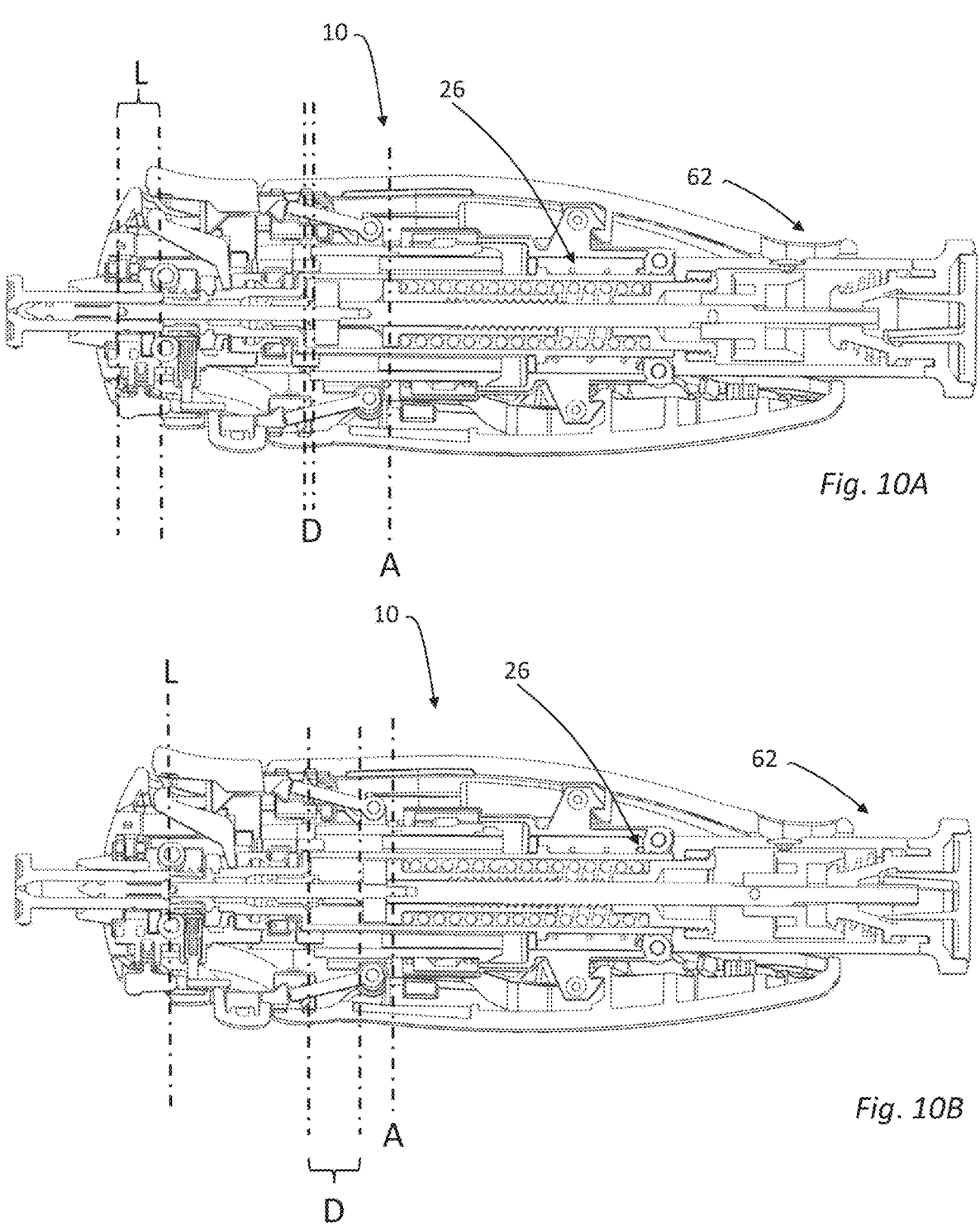
FIG. 10A is a vertical sectional view of the needle-free injector of FIG. 1, sectioned along the longitudinal centerline of the injector, with a needle-free syringe installed, the injector armed, and the dose setting apparatus set to deliver a minimum dose.
FIG. 10B is a vertical sectional view of the needle-free injector of FIG. 1, sectioned along the longitudinal centerline of the injector, with a needle-free syringe installed, the injector armed, and the dose setting apparatus set to deliver a maximum dose.
Figures 11A, 11B:
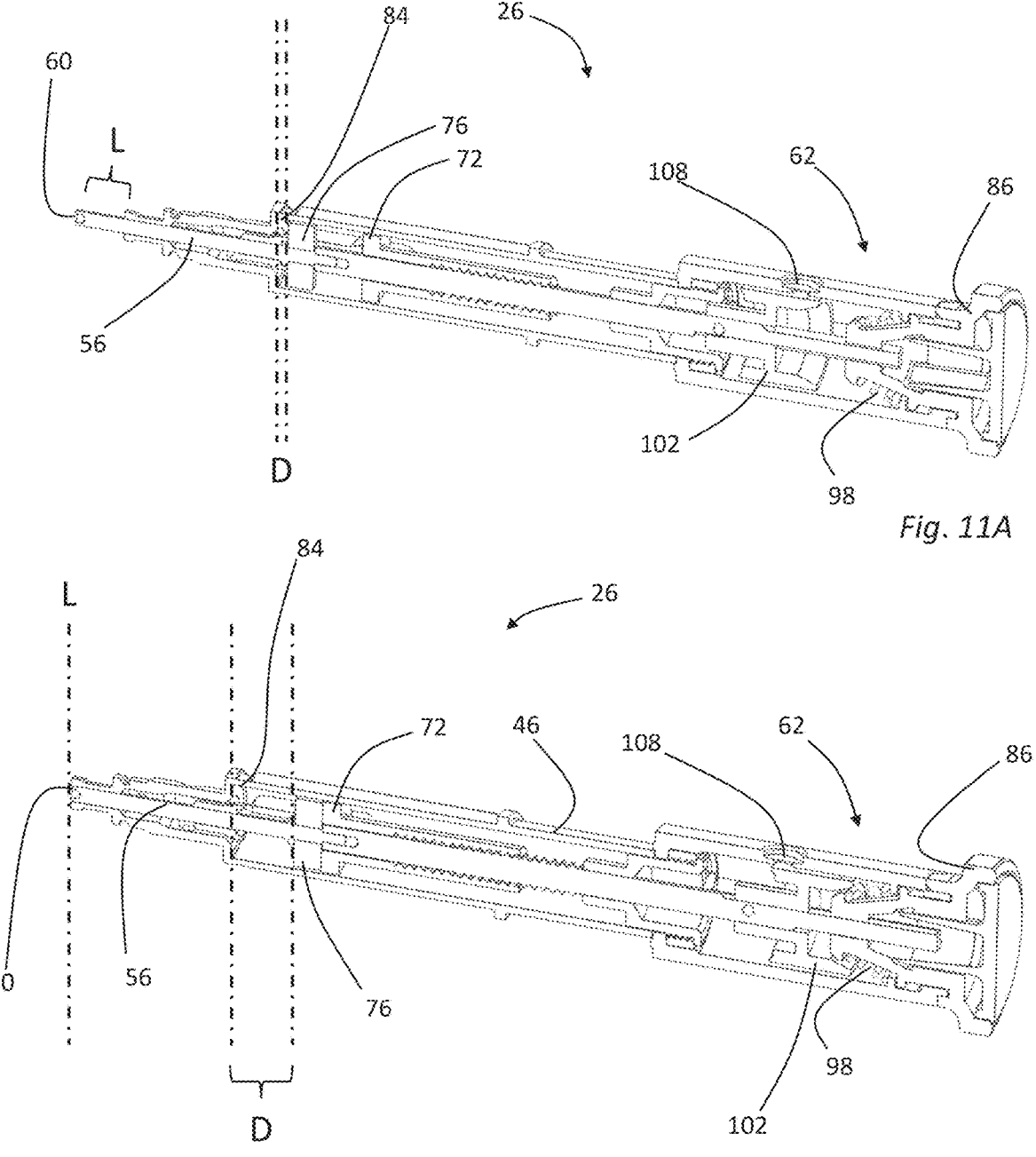
FIG. 11A is a vertical sectional view of the dose setting apparatus of FIG. 7, sectioned along the longitudinal centerline of the dose setting apparatus, with the injector armed, and the dose setting apparatus set to deliver a minimum dose.
FIG. 11B is a vertical sectional view of the dose setting apparatus of FIG. 7, sectioned along the longitudinal centerline of the dose setting apparatus, with the injector armed, and the dose setting apparatus set to deliver a maximum dose.

FIGS. 10A and 11A correspond to FIG. 4 and show the configuration of an injector 10 or a dose setting apparatus 26 configured to deliver a minimum dose. FIGS. 10B and 11B correspond to FIG. 5 and show the same injector 10 configured to deliver a maximum dose. Each of FIGS. 10A, 10B, 11A, and 11B show the injector 10 in a fully armed configuration immediately prior to injection. The dose setting steps described below may be performed prior to or after compressing the mainspring 14 and otherwise arming the injector 10. The dose setting steps may be performed before or after a filled needle-free syringe 20 is inserted into the injector syringe socket 18.

Dose setting is accomplished by manipulating the control assembly 62 of the dose setting apparatus 26. For example, the dose selector knob 86 may be rotated to cause the hammer 54 to rotate within the hammer sleeve 52 at the threaded engagement 66. Rotation of the hammer in a first direction (clockwise or counterclockwise, depending upon the threading) causes the hammer 54 to be moved forward with respect to the hammer sleeve 52. The configuration shown in FIGS. 4, 10A, and 11A shows the hammer moved fully forward, which corresponds to a minimum dose. When the hammer is placed in a forward position relative to the hammer sleeve, the length "L" the forward extension 56 of the hammer 54 extends into the opening 38 of the needle-free syringe 20 is maximized, corresponding to the minimized dose of FIGS. 4, 10A and 11A.

In the FIGS. 4, 10A and 11A configuration, it may also be noted that the hammer stopping block 76 is positioned fully forward in the stabilizing slot 74 of the hammer sleeve 52 thus, the distance "D" between the hammer stopping block 76 and the forward wall 84 of the hammer housing 46 is minimized. The distance D corresponds to the hammer stroke length when an injection is triggered since the hammer assembly 48 is driven forward by the mainspring 14 until the hammer stopping block 76 contacts the forward wall 84 of the hammer housing 46. As can be readily appreciated from FIG. 4, the distance D of this configuration directly corresponds to the relatively short length of plunger travel required to completely expel the minimized dose.

FIGS. 5, 10B and 11B show the same injector 10 after the dose selector knob 86 has been rotated in the opposite direction to move the hammer 54 fully rearward with respect to the hammer sleeve 52. This configuration corresponds to the maximum possible dose deliverable by this specific needle-free injector 10. In FIGS. 5, 10B and 11B it may be noted that the length L is minimized, and the distance D is maximized, which corresponds to a rearward initial plunger position and longer hammer stroke length required to fully expel the maximum dose deliverable by this specific needle-free injector 10.

It is important to note that FIGS. 4, 5, 10A, 10B, 11A, and 11B show a specific injector 10 set to deliver the minimum or maximum doses achievable with the illustrated apparatus. The control assembly 62 may also be manipulated to deliver any number of intermediate doses. In some embodiments the control assembly may provide for infinite, unstructured variation between the minimum and maximum achievable doses.

Alternatively, the injector 10 may include indexing structures 92 associated with the control assembly 62. The indexing structures 92 facilitate rotation of the hammer in predefined steps with each rotational step corresponding to a selected rotational angle. By controlling the pitch of the threaded engagement 66 between the hammer 54 and the hammer sleeve 52, each rotational step may also correspond to a selectable dose. Any number of intermediate doses may be defined during manufacture of an injector 10 by controlling the pitch of the threaded engagement 66, and the rotational angle(s) provided between indexed stopping points.

Figure 12A:
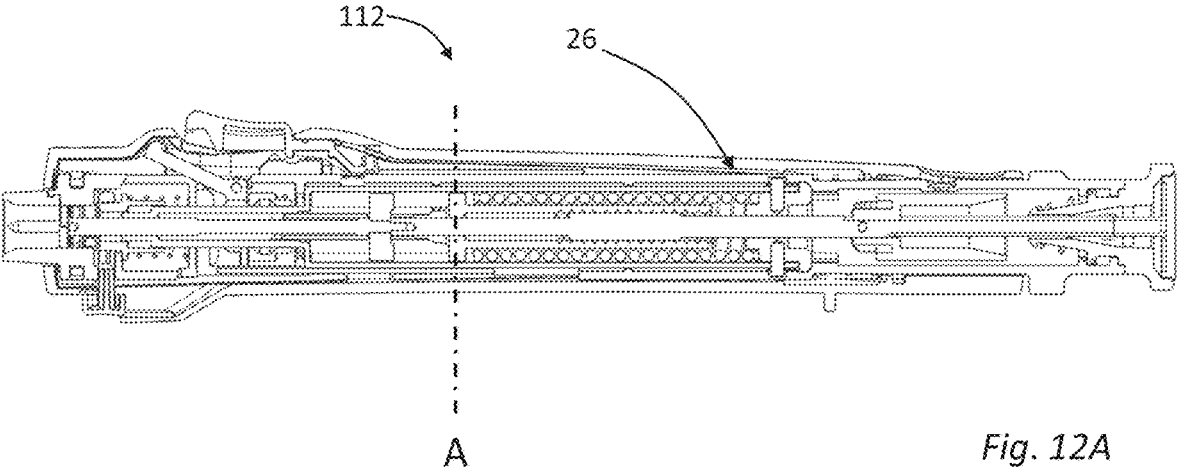
FIG. 12A is a vertical sectional view of an alternative injector embodiment, including dose setting apparatus as disclosed herein, sectioned along the longitudinal centerline of the injector, with the injector armed, and the dose setting apparatus set to deliver a minimum dose.
Figure 12B:
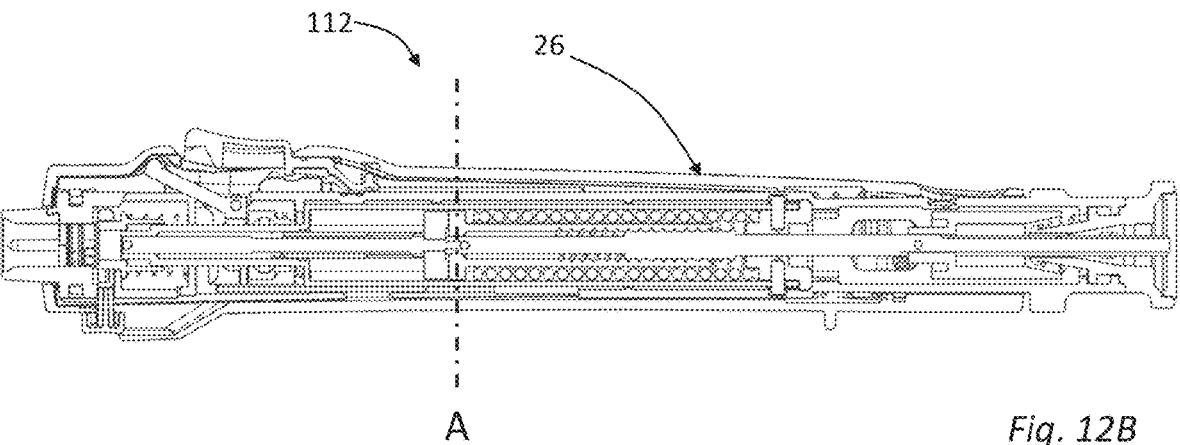
FIG. 12B is a vertical sectional view of the injector embodiment of FIG. 12A, sectioned along the longitudinal centerline of the injector, with the injector armed, and the dose setting apparatus set to deliver a maximum dose.

The injector 10 of FIGS. 4, 5, 10A, 10B, 11A, and 11B is optimized to deliver doses of between 0.02 mL and 0.1 mL into intradermal tissue layers. The dose setting apparatus 26 can be scaled to larger or smaller injectors to provide other dose ranges. For example, FIGS. 12A and 12B show a somewhat larger injector 112 optimized to deliver injections to intramuscular or subcutaneous tissues. The injector 112 includes a dose setting apparatus 26 substantially as described above, but with a relatively larger hammer assembly 48 and mainspring 14. This component scaling, typically in conjunction with a somewhat larger needle-free syringe, provides for the injector 112 to be configured to deliver a minimum dose of 0.25 mL, as shown in FIG. 12A and a maximum dose of 0.5 mL as shown in FIG. 12B. Intermediate doses are possible, as are alternative injectors having different dose ranges than those illustrated in the figures.

Figure 13A:
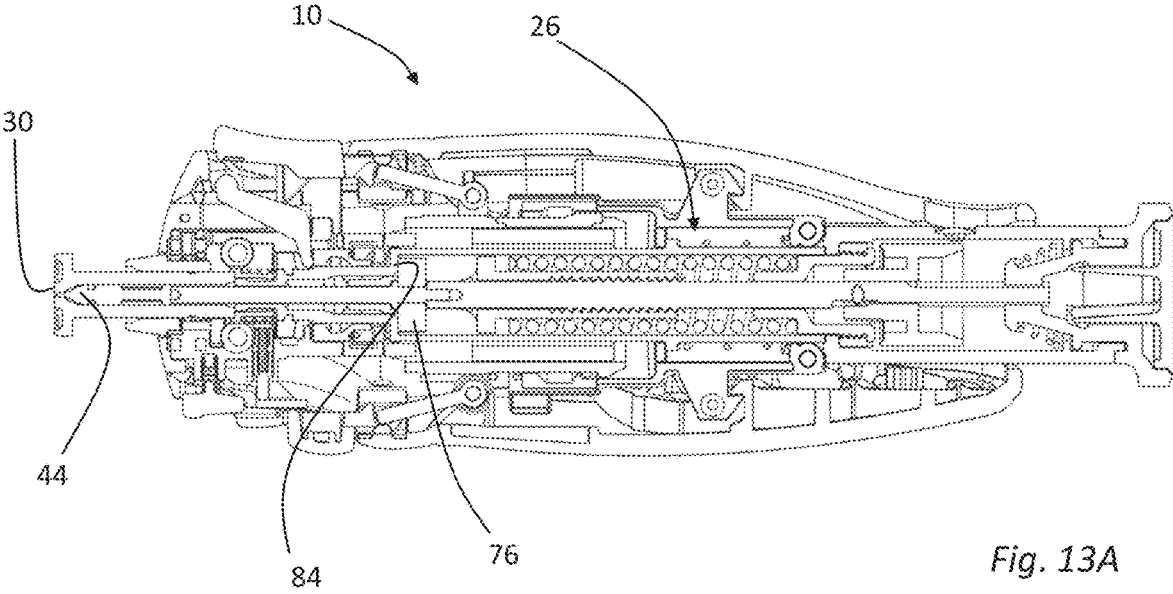
FIG. 13A is a vertical sectional view of the needle-free injector of FIG. 10A, sectioned along the longitudinal centerline of the injector, after delivery of a minimum dose.

The goal of avoiding unnecessary waste of the therapeutic injectable substance is substantially met by assuring that the forward surface 44 of the plunger 40 fully abuts the nozzle 30 of the syringe 20 as an injection is completed. Otherwise, any remaining space between the forward surface 44 and the nozzle 30 after injection would be filled with wasted injectable material. FIG. 13A shows the injector 10 minimum dose configuration of FIGS. 4, 10A, and 11A after an injection is completed. It may be noted that the hammer stopping block 76 is in contact with the forward wall 84 of the hammer housing. In addition, the forward surface 44 of the plunger 40 fully abuts the nozzle 30 within the needle-free syringe 20.

Figure 13B:
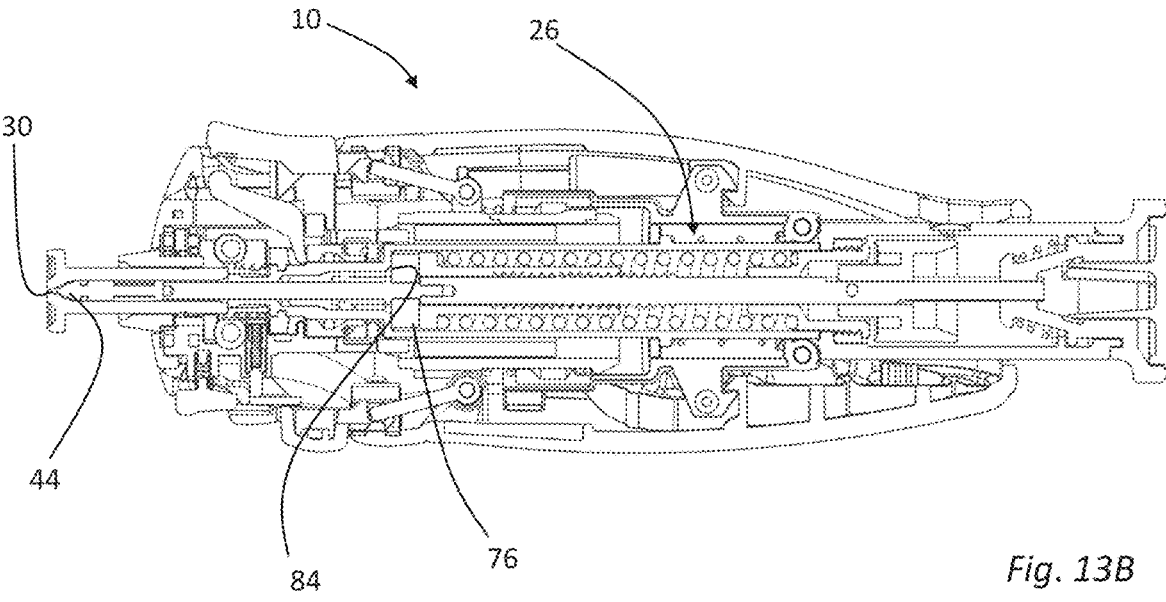
FIG. 13B is a vertical sectional view of the needle-free injector of FIG. 10B, sectioned along the longitudinal centerline of the injector, after delivery of a maximum dose.

Similarly, FIG. 13B shows the injector 10 in the maximum dose configuration of FIGS. 5, 10B, and 11B, after an injection is completed. It may be noted that the hammer stopping block 76 is in contact with the forward wall 84 of the hammer housing. In addition, the forward surface 44 of the plunger 40 fully abuts the nozzle 30 within the needle-free syringe 20. The dose setting apparatus 26 similarly causes intermediate dose settings to fully expel injectable material from the dose space 42 because at any dose setting the hammer stroke length corresponding to distance D is equivalent to the distance the plunger 40 must move within the needle-free syringe 20 to fully expel the selected dose of injectable material.

Figures 14A, 14B:
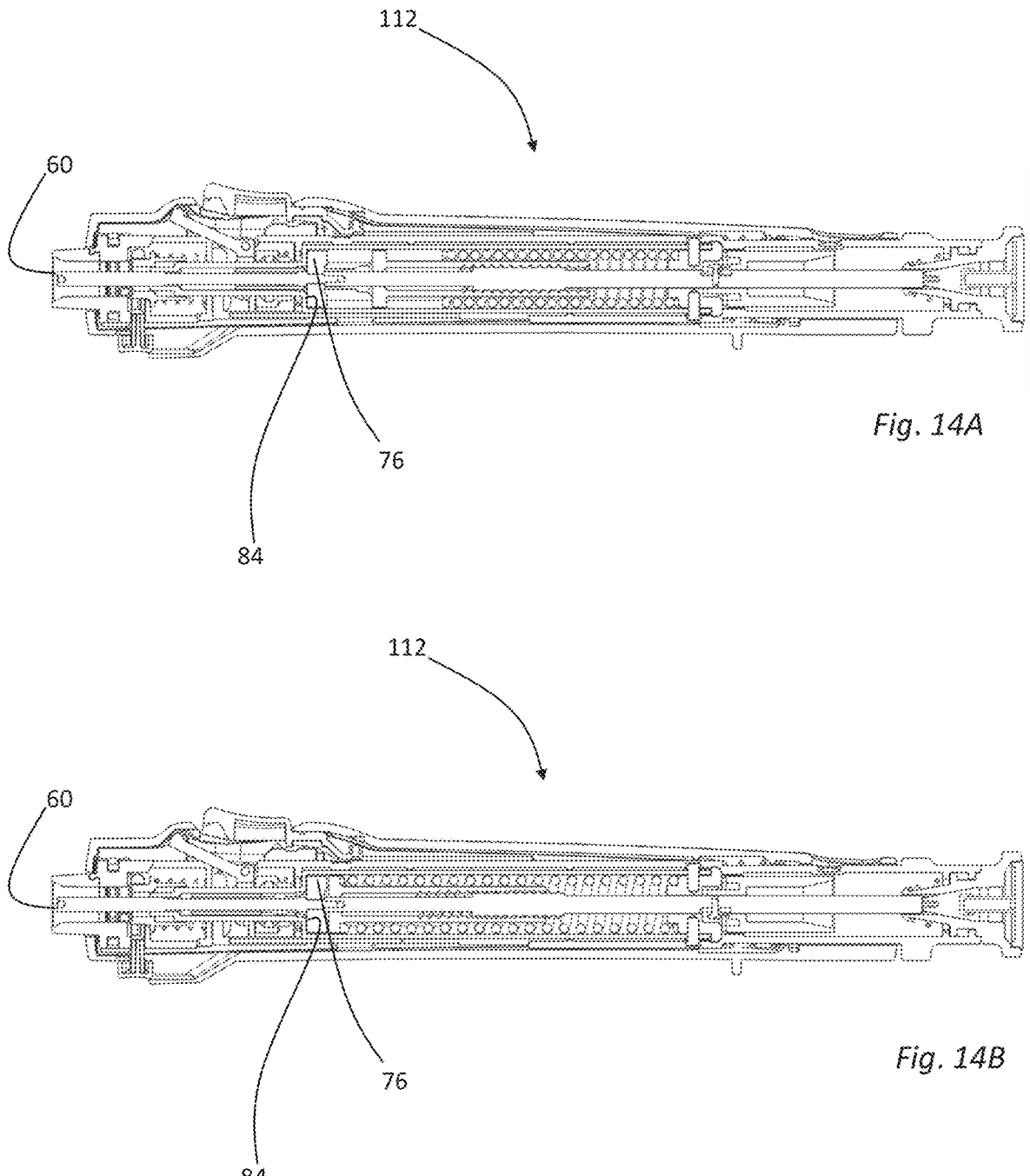
FIG. 14A is a vertical sectional view of the needle-free injector of FIG. 12A, sectioned along the longitudinal centerline of the injector, after delivery of a minimum dose.
FIG. 14B is a vertical sectional view of the needle-free injector of FIG. 12B, sectioned along the longitudinal centerline of the injector, after delivery of a maximum dose.

This attribute is present in any injector using a dose setting apparatus 26 as disclosed herein. See, for example, FIGS. 14A and 14B which show the larger injector configurations of FIGS. 12A and 12B respectively, after discharge. Although syringe and plunger elements are not shown in FIGS. 14A and 14B, it may be noted that the hammer stopping block 76 is in contact with the forward wall 84 after discharge when configured to deliver either dose. In addition, the forward surface 60 of the forward extension 56 is positioned to fully expel the injectable material from an appropriate syringe at any dose setting.

Comparison of FIG. 10A with FIG. 10B or comparison of FIG. 12A with FIG. 12B shows that the spring interface shoulder 72 of the hammer sleeve 52 is positioned at the same starting point "A" when the injector is armed at any selected dose. This configuration assures that the mainspring 14 is fully compressed according to design parameters and able to successfully deliver the selected dose to the desired tissue layers.

Some embodiments may include a status indicator 100. One type of status indicator 100 is a status sleeve 102 having a cylindrical outward facing surface 104 upon which indicia 106 may be placed. The status sleeve 102 is bonded to the rearward extension 58 of the hammer 54. Thus, the status sleeve 102 rotates with the hammer 54 and moves forward or rearward with the hammer 54. Certain indicia 106 may be visible through the window 108 in the control housing element 97. The specific indicia 106 visible at any time will depend upon the lengthwise axial position of the hammer 54 and status sleeve 102 and upon the rotational position of the hammer 54 and status sleeve 102.

For example, FIGS. 13A and 13B shown that the most rearward portion of the cylindrical outward facing surface 104 is under the window 108 after an injection has been delivered and the mainspring has driven the hammer assembly 48 as far forward as possible. This rearward portion of the cylindrical outward facing surface 104 may be surrounded by a colored band, a red band for example, to indicate to a user that the injector 10 has been discharged. Sec FIG. 15.

The status sleeve 102 will move rearward as the injector 10 is armed by and moving the hammer assembly 48 to the rear while compressing the mainspring 14. The precise axial location and angular orientation of the cylindrical outward facing surface 104 of the status sleeve 102 depends upon the dose selected since the hammer 54 is moved forward or rearward with respect to the hammer sleeve 52 when the dose is set as described above. For example, the status sleeve 102 is positioned at a relatively forward location when the injector 10 is set to deliver a minimum dose as shown in FIGS. 10A and 11A. This position causes a relatively rearward portion of the cylindrical outward facing surface 104 to be visible through the window 108. As the dose selector knob 86 is manipulated to configure the injector 10 for a larger dose, as shown in FIGS. 10B and 11B, the status sleeve 102 moves rearward along with the hammer 54. This causes a relatively forward position on the cylindrical outward facing surface 104 to be visible through the window 108. Optimization of the location of indicia 106 on the cylindrical outward facing surface 104 can, for example, cause a numeric representation of the dose selected to be shown through the window 108 when the dose has been selected and the injector 10 is armed. Sec FIGS. 16A and 16B.

Figure 17:
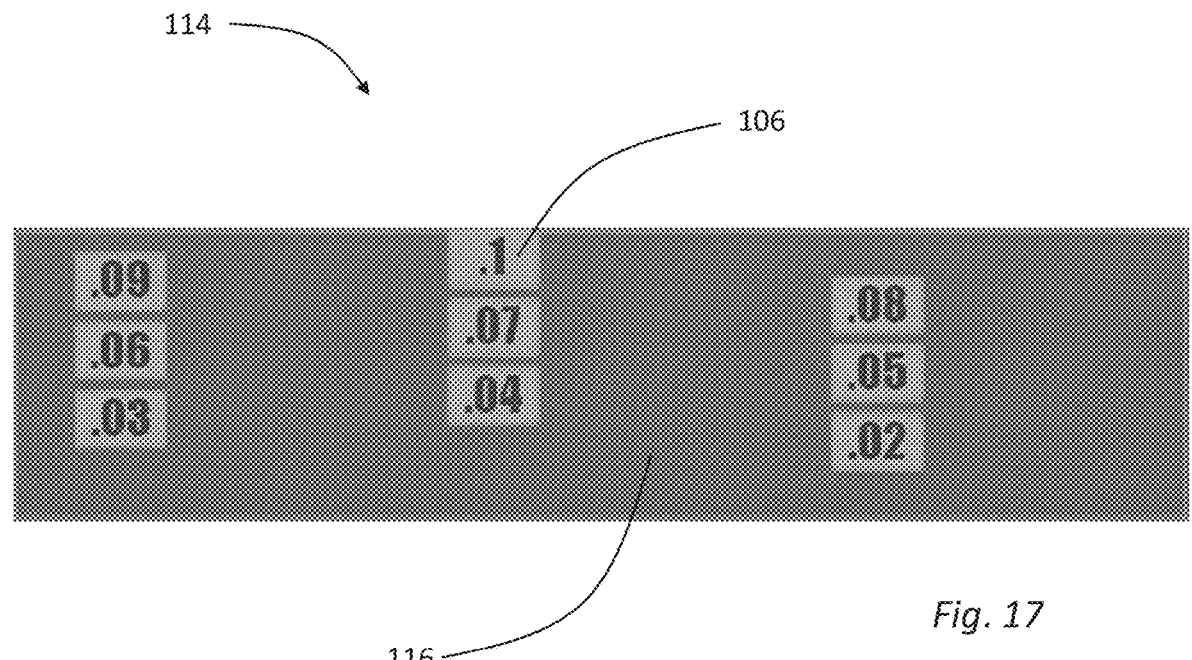
FIG. 17 is a plan view of a label including indicia showing the injector status, and the selected dose.

FIG. 17. Is a representation of a label 114 that can be applied to the cylindrical outward facing surface 104 to identify the individual doses deliverable by an indexed injector 10, such as shown in FIGS. 10A, 10B, 11A, and 11B. In this representative embodiment, the pitch of the threaded engagement 66 has been selected and formed such that rotation of the dose selector knob 86 by 120° in the first direction causes the hammer 54 to move forward within the hammer sleeve 52 a distance corresponding to a decrease of the selected dose by 0.01 mL. This injector 10 is provided with indexing structures 92 which facilitate rotation of the dose selector knob 86 in 120° increments, and which also limit unintentional further rotation. Accordingly, the label 114 is formed to wrap around the cylindrical outward facing surface 104, or otherwise be applied to the status sleeve 102 such that the proper indicia 106 is viewable under the window 108 as the dose selector knob 86 is rotated a desired number of 120° increments and the injector 10 is armed.

The indicia may include any desired type or combination of types of information. For example, the label 114 may include numeric representations of the selected dose on a green field with all other background portions 116 of the label being red. Thus, the user may see a green number indicating that the injector 10 has been set to the selected dose and armed. In all other configurations, for example, when the injector has been discharged, improperly armed, or when the dose has been incompletely set, the window will show a red indicia 106.

The indicia 106 on an infinitely variable injector embodiment could include a scale which spirals around the outward facing surface 104 from the rearward portion of the status sleeve to the forward portion of the status sleeve such that a number or mark indicating the approximate dose is always visible under the window 108 when the device has been armed.

Having described certain exemplary embodiments, it will be understood by those skilled in the art that many changes in construction and widely differing embodiments and applications of the invention will suggest themselves without departing from the scope of the present invention.

Hence, while various embodiments are described with or without-certain features for case of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A needle-free housing comprising:
a hammer housing;
a mainspring positioned within the hammer housing;
a hammer assembly engaged with the mainspring, wherein the hammer assembly comprises:
a hammer sleeve; and
a hammer engaged with the hammer sleeve, wherein the engagement between the hammer sleeve and the hammer provides for a forward or rearward position of the hammer with respect to the hammer sleeve to be changed to select an injection dose from two or more available injection doses;
a dose selector knob engaged with the hammer, wherein articulation of the dose selector knob causes the forward or rearward position of the hammer with respect to the hammer sleeve to change;
a threaded engagement between the hammer sleeve and the hammer, wherein rotation of the dose selector knob causes the hammer to rotate at the threaded engagement with respect to the hammer sleeve;
an indexing structure that becomes engaged to limit rotation of the dose selector knob when the dose selector knob is rotated through a defined angle of rotation; and
a bias spring biasing the indexing structure into engagement until the dose selector knob is displaced against the bias of the bias spring, causing the indexing structure to become disengaged.

2. The needle-free injector of claim 1 wherein the hammer sleeve comprises a spring interface shoulder.

3. The needle-free injector of claim 2 wherein the hammer comprises a hammer stopping block.

4. The needle-free injector of claim 3 wherein the hammer housing comprises a forward wall contacting the hammer stopping block when the needle-free injector is discharged.

5. The needle-free injector of claim 3 wherein the hammer comprises a forward extension extending forward of the hammer stopping block, wherein the forward extension has a fixed length.

6. The needle-free injector of claim 1 further comprising:
a status indicator defined by or attached to the hammer; and
a viewing window, through which the status indicator may be viewed.

7. The needle-free injector of claim 1 wherein the status indicator includes indicia of at least one of an arming status of the needle-free injector, and the selected dose to be delivered by the needle-free injector.

8. The needle-free injector of claim 1 further comprising a control housing element at least partially surrounding the hammer, the control housing element configured to at least partially define the indexing structure.

9. The needle-free injector of claim 8 wherein the indexing structure includes a plurality of extensions positioned on the dose selector knob, the extensions configured to mate with a plurality of gaps defined by the control housing element.

10. The needle-free injector of claim 8 wherein the control housing element includes a viewing window through which a status indicator may be viewed.

11. The needle-free injector of claim 1 wherein the indexing structure includes mating radial splines.

12. The needle-free injector of claim 1 wherein the dose selector knob includes a central socket configured to rotationally lock the dose selector knob with the hammer.

13. The needle-free injector of claim 1 wherein the dose selector knob is biased in a forward direction by the bias spring.

14. The needle-free injector of claim 1 wherein the defined angle of rotation is about 120 degrees.

15. The needle-free injector of claim 1 wherein the hammer sleeve includes female threads and the hammer includes male threads.

\* \* \* \* \*